United States Patent [19]

Kawamura et al.

[11] Patent Number: 5,371,052
[45] Date of Patent: Dec. 6, 1994

[54] PROCESS FOR RECOVERING BORON TRIFLUORIDE

[75] Inventors: Tatsuya Kawamura; Makoto Akatsu, both of Tokuyama; Hiroyasu Ishimoto, Tokyo, all of Japan

[73] Assignee: Idemitsu Petrochemical Co., Ltd., Tokyo, Japan

[21] Appl. No.: 136,341

[22] Filed: Oct. 14, 1993

[30] Foreign Application Priority Data

Oct. 19, 1992 [JP] Japan .................................. 4-280269

[51] Int. Cl.$^5$ ....................... B01J 20/34; C07C 7/00; C01B 35/00
[52] U.S. Cl. ..................... 502/20; 585/800; 585/920; 585/503; 423/276
[58] Field of Search ............... 585/800, 920, 503; 502/20; 423/276

[56] References Cited

U.S. PATENT DOCUMENTS 2,768,983  10/1956  Couper et al. .

FOREIGN PATENT DOCUMENTS 0364889  4/1990  European Pat. Off. .
0367537  5/1990  European Pat. Off. .

Primary Examiner—Anthony McFarlane
Assistant Examiner—Nhat D. Phan
Attorney, Agent, or Firm—Frishauf, Holtz, Goodman & Woodward

[57] ABSTRACT

There is provided a process for recovering boron trifluoride catalyst from an oligomerization mixture, which comprises introducing an oligomerization mixture containing catalyst comprising boron trifluoride and a complex of boron trifluoride and cocatalyst into a copper-nickel-made recovery reactor, heating the oligomerization mixture at or above a decomposition temperature of the complex, and separating and recovering boron trifluoride from the oligomerization mixture. According to the process, the boron trifluoride can be recovered effectively from the oligomerization mixture without causing the corrosion problem of the recovery reactor.

6 Claims, 1 Drawing Sheet

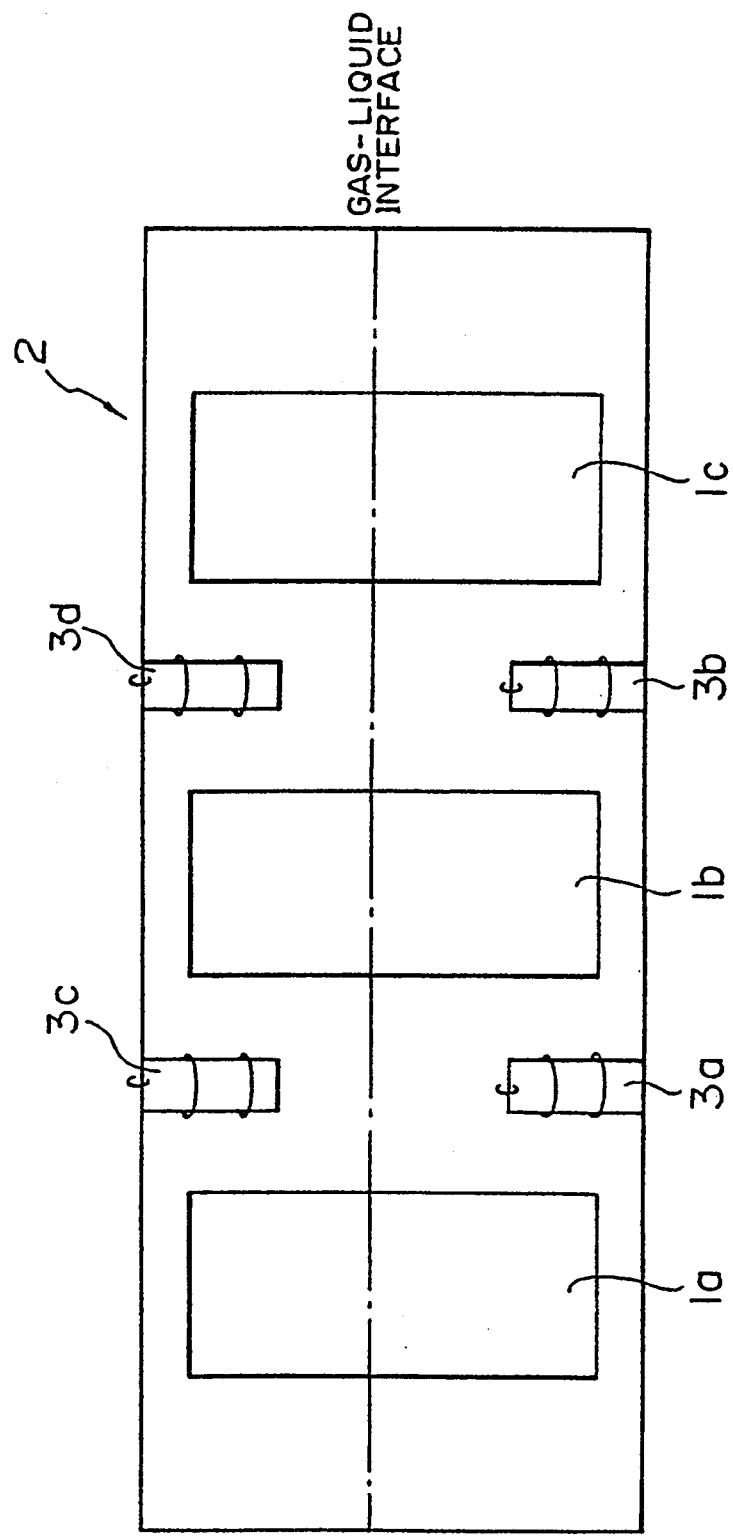

PROCESS FOR RECOVERING BORON TRIFLUORIDE

BACKGROUND OF THE INVENTION

1. Field of the Invention

The present invention relates to a process for recovering boron trifluoride of a catalyst component from an oligomerization mixture containing olefin oligomers.

2. Description of the Prior Art

An oligomer of olefin with 6-14 carbon atoms is mainly used as a base oil for synthetic lubricant. Among others, an oligomer of linear $\alpha$- olefin with 10 carbon atoms has good properties as lubricant. Thus, many processes for manufacturing it have been developed recently.

Known as one of the process for manufacturing this olefin oligomer is a method for oligomerizing an olefin with 6-14 carbon atoms in the presence of a catalyst consisting of boron trifluoride and a complex of boron trifluoride and cocatalyst. In this process, after oligomerization, the catalyst contained in an oligomerization mixture is deactivated by neutralizing the mixture with alkali solution, etc. However, as no catalyst has been recovered, lots of waste materials containing fluorine compounds and boron compounds are produced, requiring the post-treatment thereof after oligomerization.

Many processes have been proposed for recovering the catalyst contained in an oligomerization mixture. One of them is a two-step process comprising separating either boron trifluoride or a complex of boron trifluoride and coatalyst and thereafter separating the other (Japanese Laid-Open Patent Hei 2-108638). This process is advantageous inthat olefin oligomers produced cannot be deteriorated, because either of the two catalyst components has separated first to decrease the activity of the catalyst. This process is advantageous in that no corrosion is caused in the recovery treatment since it is carried out at relatively low temperature. This process, however, has a drawback that it requires a complicated apparatus for recovering the catalyst.

Known as another process, proposed is a process for recovering boron trifluoride which comprises heating an oligomerization mixture at or above a decomposition temperature of a complex consisting of boron trifluoride and cocatalyst to decompose the complex into boron trifluoride and cocatalyst, and thereafter recovering the boron trifluoride (Japanese Laid-Open Patent Hei 2-108638). In contrast to the, foregoing process, this process has an an advantage that it does not require any complicated apparatus. In this process, however, a composition of olefin oligomer tends to change during the recovery treatment of boron trifluoride. Moreover, with this process, boron trifluoride is apt to decompose and the purity of recovered boron trifluoride is lowered, leaving a problem that the boron triflouride recovered can hardly be reused as an olefin oligomerization catalyst as such.

In order to solve these drawbacks accompanying the above methods, the present inventors have found that elevating a temperature of an oligomerization mixture to 110°-155° C. in a short time prevents a composition of olefin oligomer from changing and does not cause the decrease in the purity of boron trifluoride recovered. A patent application for this method has already been filed (Japanese Patent Application Hei 4-221205). However, this process has a drawback that the corrosion atmosphere is so severe at the relatively high temperature that a recovery reactor cannot be used for a long period of time.

SUMMARY OF THE INVENTION

Accordingly, it is an object of the present invention to provide a process for effectively recovering an olefin oligomerization catalyst as boron trifluoride from an olefin oligomerization mixture without causing corrosion of a recovery reactor.

In order to accomplish this object, the present inventors have searched a material resistant to the aforementioned corrosion condition and suitable as the material of the recovery reactor. As a result, they have found that a recovery reactor composed of stainless steel, lead or copper which has been known as a corrosion resistant material showed a great corrosion rate at a relatively high temperature, for example, 110°-155 ° C. and could not be used for a long period of time, while a recovery reactor composed of copper-nickel alloy showed a very small corrosion rate even at a relatively high temperature and could be used for a greatly long period of time. They further found that an olefin oligomerization catalyst can be separated and recovered in the form of borontriluoride efficiently from a Polymerization mixture containing oligomers over a long period of time by using the recovery reactor composed of the copper-nickel alloy.

The present invention has been made based on these findings. According to the present invention, there is provided a process for recovering boron trifluoride from an olefin oligomerization mixture, comprising the steps of introducing an olefin oligomerization mixture containing olefin oligomers, which has been prepared by oligomerizing an olefin with 6-14 carbon atoms in the presence of catalyst comprising boron trifluoride and a complex of borotrifluoride and cocatalyst, into a recovery reactor of which at least an inner surface is formed with a copper-nickel alloy; heating the oligomerization mixture at or above a decomposition temperature of the complex; and separating and recovering boron trifluoride from the oligomerization mixture.

BRIEF DESCRIPTION OF THE DRAWING

The single FIGURE is a view of a polytetrafluoroethylene plate with test pieces used for a corrosion test to determine whether a sample material is suitable for a boron trifluoride recovery tank.

DETAILED DESCRIPTION OF THE PREFERRED EMBODIMENTS

The essence of the present invention resides in recovering an oligomerization catalyst in a form of boron trifluoride from an olefin oligomerization mixture containing olefin oligomers prepared by oligomerizing an olefin.

To facilitate the explanation of this essence, the description will be made with the items of (1) production of olefin oligomer by oleifin oligomerization, and then (2) separation and recovery of boron trifluoride.

(1) Production of olefin oligomer by olefin oligomerization

The olefin monomer used is limited to the one having 6-14 carbon atoms, preferably a linear $\alpha$-olefin, and most preferably 1-decene.

The catalyst used includes boron trifluoride and a complex of boron trifluoride and cocatalyst. The examples of the cocatalyst are as follows:
a) water
b) alcohols; methanol, ethanol, n-butanol, decanol
c) carboxylic acids; acetic acid, propionic acid, butyric acid
d) ethers; dimethyl ether, diethyl ether
e) acid anhydrides; aceticanhydride, succinic anhydride
f) esters; ethyl acetate, methyl propionate
g) ketones; acetome, methyl ethyl ketone
h) aldehydes; acetaldehyde, benzaldehyde The above catalyst can be employed solely or in combination of two or more n-butanol is the most preferable.

The complex of boron trifluoride and cocatalyst is used commonly in an amount of 0.05–10.0 vol. %, preferably 0.1–5.0 vol. % per olefin. Only small amount of boron trifluoride is necessary in an oligomerization system. Such amount of boron trifluoride is 0.01–2 times, preferably 0.1–1.5, times as much as a saturation concentration of boron trifluoride in the olefin oligomer at atmospheric pressure.

At an initial stage of oligomerization, it is desirable to keep boron trifluoride concentration lower than the saturation concentration in the olefin oligomer at atmospheric pressure so as to restrict exotherm. On the contrary, at a later stage of oligomerization it is desirable to keep boron trifluoride concentration at or above the saturation concentration in the olefin oligomer at atmospheric pressure so as to accelerate the oligomerization.

While an oligomerization temperature, oligomerization pressure and oligomerization time are not critical, the oligomerization temperature is set for $-20°$ to $90°$ C., preferably $0°$ to $50°$ C., the oligomerization pressure is set for 0 to 35 kg/cm2G, preferably 0.05 to 5 kg/cm2G, and the oligomerization time is set for 0.25 to 24 hours, preferably 2 to 16 hours.

An oligomerization method may be either batch method or continuous process. Generally, boron trifluoride is supplied continuously to the oligomerization system during the oligomerization.

(2) Separation and Recovery of Boron Trifluoride

In the process for recovering boron trifluoride according to the present invention, the oligomerization mixture in the above item (1) is introduced into a recovery reactor of which at least an inner surface is formed with a copper-nickel alloy; the oligomerization mixture is heated at or above a decomposition temperature of a complex of boron trifluoride and cocatalyst; and thereafter the boron trifluoride is separated and recovered from the oligomerization mixture. The item (a) material of a recovery reactor and the item (b) a heating condition are important in the present method. These items will be explained individually.

(a) Material of a recovery reactor

According to the invention' investigation, when a copper-nickel alloy is used as a material of a recovery reactor, it exhibits a very small corrosion rate even under a severe condition wherein the oligomerization mixture containing boron trifluoride and a complex of boron trifluoride and cocatalyst is in contact with the inner surface of the recovery reactor at a relatively high temperature such as $80°$–$180°$ C. On the contrary, each of stainless steel, copper and lead conventionally used as a corrosion-resistant material shows an considerably large corrosion rate under the same condition.

Consequently, employing the copper-nickel alloy for a recovery reactor makes it possible to use such a recovery reactor for a long period of time, contributing to industrial need. Such copper-nickel alloy can be a cupronickel, etc. containing preferably 90–60 wt. % of copper and 10–40 wt. % of nickel. The above specified content of copper and nickel accomplishes a small corrosion rate and low construction cost of the recovery reactor.

Whereas it is necessary to use the copper-nickel alloy for at least an inner surface of the recovery reactor, generally the whole recovery reactor is made of such copper-nickel alloy. Usually an oligomerization mixture containing olefin oligomers is continuously introduced into the recovery reactor.

(b) Heating condition

The oligomerization mixture containing olefin oligomers introduced into the recovery reactor is heated at or above a decomposition temperature of a complex of boron trifluoride and cocatalyst. For effectively recovering high purity boron trifluoride, it is preferable to heat and maintain the olefin oligomer-containing mixture in the recovery reactor preferably at $80°$–$180°$ C., and most preferably at $110°$–$155°$ C. If the temperature is lower than $80°$ C., the decomposition of a complex of boron trifluoride and cocatalyst becomes slower with a rapid decrease of recovery rate and the oligomerization mixture changes its composition or properties.

On the other hand, if the temperature exceeds $180°$ C., the recovery rate scarcely increases and the purity of boron trifluoride decreases.

The oligomerization mixture is heated in a recovery reactor equipped with a heating jaket and an agitator. The heating of the mixture with agitating keeps the temperature of the mixture at a predetermined temperature.

The oligomerization mixture may be introduced into a recovery reactor after it is heated with a heat exchanger. In this case, an agitator may be unnecessary in the recovery reactor. A tube-shell type heat exchanger having a carbon-made tube might be preferable for the heat exchanger.

It is desirable that the temperature elevation to a complex decomposition temperature or above at an initial stage of heating is conducted as rapidly as possible so as to avoid the change of composition or properties of the oligomerization mixture. The boron trifluoride separated and recovered through such heat treatment has high purity and it can be recycled and reused directly.

The present invention will be further explained with the following examples.

EXAMPLE 1

(Preparation of 1-decene oligomers)

All experiments of preparation of oligomers were carried out using two 1 litter continuous stirred tank reactors in series. An oligomerization pressure and temperature were set at atmospheric pressure and at $20°$ C., respectively, in each reactor. The residence time was controlled to 2.2 hours in the first reactor and 1.0 hour in the second reactor. The catalyst was boron trifluoride and a complex of trifluoride and n-butanol.

1-Decene, the boron trifluoride and the above complex were supplied to the first reactor. The amount thereof supplied are shown in Table 1 below. The oligomerization mixture from the first reactor was introduced directly into the second reactor.

The composition of 1-decene oligomers obtained in this example is also shown at Table 1.

TABLE 1

| Amounts Supplied | 1-Decene | 400 ml/h |
|---|---|---|
| | BF₃ | 267 ml/h |
| | Complex of BF₃ and n-BuOH | 2 ml/h |
| Composition of Oligomerization Mixture Produced | C10, C20 (1-Decene and Oligomer with 20 carbon atoms) | 4 wt. % |
| | C30 (Oligomer with 30 carbon atoms) | 23 wt. % |
| | C40 (Oligomer with 40 carbon atoms) | 38 wt. % |
| | C50+ (Oligomers with 50 or more carbon atoms) | 35 wt. % |

Recovery of Boron Trifluoride

The test pieces of cupronickel (Cu: 70 wt. %, Ni: 30 wt. %) as a copper-nickel alloy were mounted and fixed to polytrafluoroethylene plate. The manner the test pieces were mounted is illustrated in the single FIGURE. First, two rectangular polytetrafluoroethylene plates 2 with cutouts 1a, 1b and 1c were prepared. Each of the cupronickel pieces 3a, 3b, 3c, 3d were fixed with a corrosion-resistant threads inserted through small holes formed near the test pieces-fixing sites of the polytetrafluoroethylene plate 2. The reason why two pairs of test pieces are fixed at the different sites is that when the polytetrafluoroethtlene plate 2 was located at a predetermined level in the recovery reactor, one pair of pieces 3a, 3b were immersed in the liquid and the other pair of pieces 3c,3d stayed in a vapor phase.

The polytetrafluoroethylene plate 2 with the test pieces 3a, 3b, 3c and 3d was rounded into a cylinder form and was placed along an inner wall of a cylindrical polytetrafluoroethylene recovery reactor (inner diameter: 100 mm, height: 180 mm). This recovery reactor was equipped with an agitator, gas exhaust pipe, liquid level controller and heater.

The oligomerization mixture running off the second reactor was continuously introduced into the recovery reactor and heated at 110°, 130° and 150° C., respectively, at each test by the heater set at a body of the recovery reactor.

By heating and maintaining the mixture at the above temperature, the complex of boron trifluoride and n-butanol was decomposed and boron trifluoride was produced. The boron trifluoride produced was discharged from the recovery reactor through the exhausts pipe. The boron trifluoride had a purity sufficient to be recycled and reused directly.

The oligomerization mixture was continuously discharged through a liquid drainage pipe disposed at the bottom of the recovery reactor. The residence time of the mixture was in the recovery reactor was controlled to 1.5 hours.

After a predetermined test time, the polytetrafluoroethylene plate 2 with test pieces 3a,3b,3c and 3d was taken out of the recovery reactor. After the test pieces 3a–ed were washed with acetone and then dried, their weights were measured. The corrosion rate of the test piece was calculated as below:

$$\text{Corrosion Rate (mm/yr)} = \frac{[A \text{ (mg)} \times 24 \times 365 \text{ (h/yr)} \times 10]}{[B \text{ (cm}^2\text{)} \times C \text{ (h)} \times D \text{ (mg/cm}^3\text{)}]}$$

{where A is weight decrease of the test piece (mg), B is a surface area of the test piece (cm²), C is a dipping time (h) and D is a density of the test piece (mg/cm³)}

The test results are shown in Table 2 below.

TABLE 2

| Test Piece Material | Temperature (°C.) | Time (h) | Corrosion Rate (mm/year) |
|---|---|---|---|
| Cupronickel | 110 | 70 | $1.8 \times 10^{-1}$ |
| | | 160 | $8.5 \times 10^{-2}$ |
| | 130 | 70 | $2.5 \times 10^{-1}$ |
| | | 160 | $9.8 \times 10^{-2}$ |
| | 150 | 70 | $1.7 \times 10^{-1}$ |
| | | 160 | $7.4 \times 10^{-2}$ |

The above test results are for the cupronickel test pieces 3a and 3b dipped into the liquid in the recovery reactor. It is observed that the corrosion rates are very small at any temperature. Thus, the cupronickel has proved to be a very suitable and practical material for the boron trifluoride recovery reactor.

Almost no corrosion was observed for the test pieces 3c and 3d placed in the vapor phase of the recovery reactor.

COMPARATIVE EXAMPLE 1

The tests were carried out in the same manner as in Example 1 except that test pieces each of which was made of SUS 316 (a kind of stainless steel), copper or lead were used instead of cupronickel used in Example 1. The corrosion rates were measured like Example 1. The test results are shown in Table 3 below.

TABLE 3

| Test Piece Material | Temperature (°C.) | Time (h) | Corrosion Rate (mm/year) |
|---|---|---|---|
| SUS 316 | 130 | 70 | $4.1 \times 10^0$ |
| | | 160 | $3.9 \times 10^0$ |
| Copper | 130 | 70 | $7.1 \times 10^{-1}$ |
| | | 160 | $5.3 \times 10^{-1}$ |
| Lead | 130 | 70 | $7.9 \times 10^0$ |
| | | 160 | $7.2 \times 10^0$ |

Referring to Table 3, all of the SUS 316, copper and lead show the corrosion rates much higher than that of the cupronickel used in the present invention. Therefore, it is clear that they are improper materials for the boron trifluoride recovery reactor.

According to the preceding explanation, it is understood that the present invention provides an efficient process for efficiently separating and recovering an oligomerization catalyst in the form of boron trifluoride from an oligomerization mixture without causing the causing the corrosion problem of the recovery reactor.

What is claimed is:

1. A process for recovering boron trifluoride from an olefin oligomerization mixture containing olefin oligomers, comprising the steps of:

introducing an olefin oligomerization mixture containing olefin oligomers, which has been prepared by oligomerizing an olefin with 6–14 carbon atoms in the presence of catalyst comprising boron trifluoride and a complex of boron trifluoride and cocatalyst, into a recovery reactor of which at least an inner surface is formed with a copper-nickel alloy;

heating the oligomerization mixture at or above a decomposition temperature of the complex; and separating and recovering boron trifluoride from the oligomerization mixture.

2. The process according to claim 1, wherein the oligomerization mixture is introduced to the recovery reactor maintained at a temperature of 80°–180° C.

3. The process according to claim 1, wherein the copper-nickel alloy contains 90–60 wt. % of copper and 10–40 wt. % of nickel.

4. The process according to claim 1, wherein the recovery reactor is totally made of the copper-nickel alloy.

5. The process according to claim 1, wherein the oligomerization mixture is heated and maintained at 80°–180° C.

6. The process according to claim 1, wherein the oligomerization mixture is heated and maintained at 100°–155° C.

* * * * *